United States Patent [19]

Muxfeldt et al.

[11] 4,268,495

[45] May 19, 1981

[54] INJECTABLE EMBOLIZATION AND OCCLUSION SOLUTION

[75] Inventors: Hans Muxfeldt, Norderstedt; Hermann Dahlke, Hamburg, both of Fed. Rep. of Germany

[73] Assignee: Ethicon, Inc., Somerville, N.J.

[21] Appl. No.: 1,802

[22] Filed: Jan. 8, 1979

[51] Int. Cl.$^3$ .................. A61K 29/00; G01N 33/48
[52] U.S. Cl. ............................ 424/1; 128/659; 260/112 R; 424/1.5; 424/9
[58] Field of Search ............... 424/1, 99, 1.5; 260/112 R; 128/653, 654, 659

[56] References Cited

PUBLICATIONS

Mosse, Chem. Abstracts, vol. 66, 1967, abstract number 8283g.

Bonadeo, Chem. Abstracts, vol. 72, 1970, abstract number 88767a.

Ikegami et al, Chem. Abstracts, vol. 84, 1976, abstract number 104185q.

Thelen et al, Forschr. Rontgenstr., 124(3), 1976, pp. 232-235.

*Primary Examiner*—Benjamin R. Padgett
*Assistant Examiner*—Christine M. Nucker
*Attorney, Agent, or Firm*—Wayne R. Eberhardt

[57] ABSTRACT

An injectable embolization and occlusion solution for the selective closure of organs, their duct systems, or blood vessels, comprises a solution of a prolamine such as zein in a physiologically compatible solvent such as ethanol. The solution is injected into the site to be treated where the prolamine quickly precipitates in the body fluids to occlude the site area.

15 Claims, No Drawings

INJECTABLE EMBOLIZATION AND OCCLUSION SOLUTION

BACKGROUND OF THE INVENTION

The present invention relates to an injectable embolization and occlusion solution, which serves for the selected closure of organs, their duct systems, or blood vessels, and is introduced to the required site in a simple way with the aid of cannulas, catheters, endoscopes, or suitable applicators under X-ray control, and is precipitated there in the aqueous medium, in order to stop the flow of secretions from, or the flow of blood to, the appertaining organs or parts of an organ, staunch acute internal bleeding, completely obliterate pathologically modified sections of vessels, or temporarily or definitively block these or fill them with a biological material. If a radioactive substance or an artificial isotope such as $^{133}I$ with a suitable half-life and/or a cytostatic agent are added to the solution according to the invention, then the therapeutic effect obtained by cutting off the blood supply in the embolization of blood vessels supplying a tumor is reinforced by the fixed radioactive substances and cytostatic agents, distributed in the entire arterial tree. The addition of an artificial isotope with a shorter halflife can serve the purpose of not only radiation therapy but also of diagnosis.

Occlusion of the pancreatic ducts for the separate elimination of the secretory function of the pancreas has so far been possible only by a transduodenal suture of the orifice of the ductus pancreaticus with a purse-string ligature, with subsequent plastic shaping of the papilla, or else by a complete pancreaticoduodenectomy, with the relevant associated interventions. Attempts have also been made to effect the transduodenal occlusion of the terminal section of the ductus pancreaticus by the injection of a plastic. The operations for the treatment of chronic and acute pancreatitis place a very great strain on the patients and cannot be done at an advanced age. The ligation of the ductus pancreaticus has led to acute pancreatitis in most cases; the occlusion with a plastic has not yet been fully successful without the occurrence of side effects. Another disadvantage of both methods is that pancreatic fistulas can be formed after the removal of biopsy samples for differential diagnosis (chronic pancreatitis-pancreatic carcinoma).

Arterial catheter embolization has so far been carried out in the case of renal carcinoma (preoperatively and palliatively), gastrointestinal bleeding, renal bleeding (arteriovenous fistulas), pelvic fracture, bone tumors, varicose bleeding, vaginal bleeding (in the case of portio carcinoma), and intracerebral arteriovenous fistulas.

The ideal embolizing material is not yet available. A wide variety of substances have been used, such as autologous thrombi, plastics, synthetic substances (e.g., polystyrene, polyurethanes, polyvinyl alcohol, or silicone resins), autologous muscle fibers, fat, fibrin foam, gelatin foam, alkyl cyanoacrylates and isopropyl palmitate [cf. M. Thelen et al., Fortschr. Rontgenstr. 124(3), 232–35 (1976)]. In practice, these substances have been found unsatisfactory in their technical application. The introduction of solids with the aid of a catheter is difficult. The absence of X-ray contrast media makes monitoring problematic. In the case of alkyl cyanoacrylate monomers, it is difficult to control spontaneous polymerization.

The aim of the present invention is to provide an injectable embolization and occlusion solution, which is applied at the right viscosity and then made to solidify at the required site in the vessel. This is done on the basis of the surprising discovery that, when a solution containing a substantial amount of a prolamine is used, reliable closure of organs, their duct systems, or blood vessels is obtained without the occurrence of side effects. Another aim of the present invention is to provide a process for the closure of organs, their duct systems, or blood vessels in animals and man with the aid of an injectable embolization and occlusion solution, which process ensures a reliable closure without the occurrence of side effects.

DESCRIPTION OF THE INVENTION

The embolization and occlusion solution is prepared in practice as follows.

The physiologically compatible solvent—preferable a mixture of water and an alcohol with 2–5 carbon atoms—is made ready for use. If a contrast medium, a cytostatic agent, an antimicrobial substance, or a specific pancreas inhibitor is to be used, it is added to the solvent in the required amount. The prolamine is dissolved in the solvent with careful stirring. The pH of the solution is adjusted to about 6.5–6.8 and preferably to about 6.65, with a physiologically compatible acid or base. The density of the solution at 25° C. is about 1.05–1.1 and preferably 1.08 g/ml. The viscosity of the solution at 25° C. is about 350–800 and preferably 400–500 centipoise. The viscosity is checked after 12–14 hrs. If the viscosity of the solution is to be raised, a physiologically compatible oil is added at this point, with careful stirring. The solution is then ready for use and can be poured, e.g., into ampuls or small bottles. Directly before the filling operation, a conventional sterilizing agent such as propylene oxide may be added to the solution.

In experiments in which the solution according to the invention was injected into the ductus pancreaticus no pancreatic fistula has yet occurred in any of the cases.

In the case of an infected duct system closure of the duct is not possible because of the risk of acute pancreatitis. When a pancreatic cyst is present there is a danger that it will be enlarged and will rupture.

None of the disadvantages mentioned here occurred when the solution according to the invention was used in animal experiments. The pancreas treated in this way never developed acute pancreatitis. The pancreatic tissue reformed without any change in the structure and function of the islet cells. In contrast to the case of complete pancreaticoduodenectomy, where the island organ is removed, only in very rare cases has the long-term treatment of diabetes that develops been successful.

Pancreatitis was produced by artificial infection in animal experiments on dogs. It was found, surprisingly, that the symptoms rapidly disappeared after the occlusion of the infected pancreas by the introduction of the solution according to the invention. The first clinical trails on human subjects indicate that the therapy of pancreatitis in man is also possible.

Prolamines form the main protein components of cereal grains and flour. Unlike all other proteins, they can be extracted from flour with 80 percent alcohol, but they are insoluble in absolute alcohol and water. The most important prolamines are zein, gliadin, and hordein. Zein is preferred in the present invention.

The prolamine, preferably zein, can be used in an amount of 3-60 and preferably 5-45 wt percent.

It has been found, surprisingly, that the solution according to the present invention, which contains a prolamine, is particularly suitable, because prolamines are physiologically harmless substances that can be applied in the liquid form with an adjustable viscosity and then solidify at the required site in the vessel.

Unlike all other proteins, prolamines are soluble in dilute alcohols and other solvents, but they are insoluble in water. Examples of solvents for prolamines are $C_2$–$C_5$ alcohols (methanol dissolves them only to a small extent and denatures them), ethylenediamine, 1-acetylpiperidine, ethylene glycol, propylene glycol, glycerol, N-methylacetamide, formamide, hydrazine, dimethylformamide, and dimethyl sulphoxide. When choosing the solvent for the occlusion solution according to the invention, the optimal suitability of the solvent as regards its physical properties and precipitation mechanism must be weighed against its possible toxicity. The preferred solvent is a mixture of ethanol and water, and the amount of water can vary between 4 and 50 percent, according to how quickly the prolamine is to precipitate out.

In ethanol, prolamines form viscous and slightly thixotropic solutions. At a constant prolamine content, the viscosity of the solutions increases with increasing ethanol concentration (see Table I).

At a constant ethanol concentration, the viscosity increases with increasing concentration of the prolamine (Table II).

TABLE I

| Viscosity of a 35% w/v Zein Solution in 50-95% v/v Ethanol | |
|---|---|
| Ethanol %, v/v | cp (25° C.) |
| 95 | 790 |
| 90 | 750 |
| 85 | 730 |
| 80 | 705 |
| 75 | 685 |
| 70 | 660 |
| 65 | 640 |
| 60 | 600 |
| 55 | 490 |
| 50 | 340 |

TABLE II

| Viscosity of 5-40% w/v Zein Solutions in 60% v/v of Ethanol | |
|---|---|
| Zein %, w/v | cp (25° C.) |
| 5 | 5 |
| 10 | 15 |
| 15 | 38 |
| 20 | 78 |
| 25 | 160 |
| 30 | 265 |
| 35 | 475 |
| 40 | 785 |

Prolamines are decomposed into amino acids by hydrolytic cleavage. The analysis of a zein hydrolysate shows that zein contains substantial quantities of glutamic acid (23%), leucine (19%), proline (9%), and L-alanine (9%), but no lysine or tryptophan. Being proteins, prolamines are expected to be absorbed by the body in vivo, and this has in fact been confirmed in animal experiments on rats and rabbits. Small rods made of zein, with a length of 1-2 cm, were implanted intramuscularly, and both the adsorption and the tissue reactions were compared with those observed after implantation of catgut. The results showed that the prolamine zein is absorbed in about the same period of time, 4-6 weeks, as cutgut, and this process is accompanied by leucocyte infiltration, which seems to be slightly more extensive in the case of zein. It has been found, however, that this is not due primarily to zein but to impurities present in commercial prolamines. In particular, it is necessary to remove the coloring matter of zein, i.e., 3,3'-carotenediol, by boiling in petroleum ether.

Prolamines differ in their behavior to some extent according to the species and the variety of the cereal and the conditions under which the plants grow and ripen. This circumstance must be taken into account when making up a preparation. The decisive factor is not a fixed concentration but a certain viscosity of the prolamine in the solvent used.

The molecular weight of prolamines is 25,000-40,000. The viscosity of a prolamine solution is undoubtedly connected with the molecular weight, but so is also the time of absorption. By crosslinking with tanning substances such as chromic acids, formaldehyde and glutaric dialdehyde, the time of absorption can be increased as desired; this also changes the solubility of the prolamines and the properties of the gels made from them. Treatment with ionizing radiation (2.5 Mrad) does not provoke recognizable undesirable changes in prolamines. Even the viscosity of prolamine solutions remains unchanged. Irradiation with gamma rays is the preferred way to sterilize such solutions. However, the addition of liquid propylene oxide (0.5-1.0% w/v) to prolamine solutions in a mixture of ethanol and water also ensures a satisfactory sterility without changing the consistency and the compatibility.

In catheter embolization with prolamine solutions the aim is to adjust the viscosity of the solution to the highest possible value, so as to prevent the escape of the prolamine solution through the capillaries and into the venous system. Furthermore, the water content of the mixture of water and solvent must be as high as possible, so that the prolamine is precipitated as quickly as possible when it comes into contact with the aqueous medium of blood. The solutions must be thin enough to be applicable through catheters (2-4 Charr.). Cohesion and adhesion must be so controlled that no drawn "thread" is formed when the catheter is being withdrawn after the embolization, and the embolus does not adhere to the catheter. This can be ensured by the addition of a physiologically compatible oil. An example of such oils is peanut oil, which considerably increases the viscosity of the solution of prolamines in ethanol-water mixtures if the amount of prolamine is kept constant with respect to the amount of solvent (see Table III), and even substantially more if the prolamine content is kept constant with respect to the total amount of the preparation.

Vegetable oils are particularly suitable because they are physiologically harmless and are metabolized in the body. Examples of oils that can be used are peanut oil, olive oil, poppyseed oil, and almond oil. The amount of oil in an occluding solution according to the invention can be between 5 and 45% w/w. The oil is added to the prolamine solution after the prolamine has been completely dissolved. The use of an emulsifier is not necessary, because prolamines have a certain emulsifying action.

TABLE III

Viscosity of 35% w/v Zein Solutions in 60% v/v Ethanol After the Addition of Various Amounts of Peanut Oil

| Amount of peanut oil added %, w/w | cp (25° C.) |
|---|---|
| 0 | 450 |
| 15 | 710 |
| 25 | 890 |
| 35 | 1200 |
| 45 | 1450 |

The increase in viscosity depends on the viscosity of the oil added, which in turn depends on the melting point. For example, the addition of the same amount of poppyseed oil and peanut oil to a certain solution of a prolamine in aqueous ethanol leads to different viscosities. Such additions of oil do not only affect the viscosity, but also reduce the adhesion and the internal elasticity of the prolamine solution. This can be demonstrated on the change in the dripping rate (number of drops per minute) and the weight of the droplets when pouring zein solutions containing different amounts of oil (see Table IV).

TABLE IV

Dripping Rate and Droplet Weight of Zein Solutions with Different Poppyseed Oil Contents

| Poppyseed oil %, w/w | Drops/min | Droplet weight mg |
|---|---|---|
| 5 | 32 | 21 |
| 15 | 24 | 20 |
| 25 | 20 | 18 |
| 35 | 16 | 18 |
| 45 | 12 | 16 |

The breaking-off at the catheter after the occlusion of the vessel can thus be optimized by an appropriate choice of the nature and the proportions of the components.

The addition of an oil also has another significance. Prolamines in solution precipitate out in an aqueous medium in the form of relatively solid blocks. When the solutions contain emulsified oils, however, oil globules are trapped in the precipitated prolamine block, imparting to it a porous structure. This makes it easier for the body's connective tissues to proliferate over them during the absorption process. There is a quicker organization of the embolus which ensures a definitive closure of the vessel and excludes any recanalization.

Compounds that are soluble in water and in the solvent of the prolamine and are customarily employed in angiography can be used as X-ray contrast media, examples being sodium amidotrizoate (sodium N,N-diacetyl-3,5-diamino-2,4,6-triiodobenzoate); 5-acetamino-2,4,6-triiodoisophthalic acid methyl amide-3; sodium acetrizoate (sodium 3-acetamino-2,4,6-triiodobenzoate) and sodium 2-iodohippurate. These do not change the basic characteristics—and especially the viscosity—of prolamine solutions (see Table V).

The contrast medium enclosed in the precipitated prolamine block makes an X-ray control of the occlusion possible not only during the application but also at later times, in order to check its efficiency and the changes that have occurred.

TABLE V

Viscosity of a 35% w/v Zein Solution in a 60% v/v Ethanol After the Addition of Various Amounts of an X-ray Contrast Medium (Sodium Amidotrizoate)

| Contrast medium (sodium amidotrizoate) %, w/v | cp (25° C.) |
|---|---|
| 10 | 780 |
| 20 | 780 |
| 30 | 800 |
| 40 | 810 |

When long-term X-ray control is planned or desirable and the site favors the escape of the soluble contrast medium by diffusion, as for example, in the case of a partial palliative renal embolization, one can use water-insoluble contrast media such as barium sulphate or the contrast media mentioned above but in the acid form instead of the form of sodium salts. To prevent the sedimentation of the particles in the solution, an accurate control of the particle size is therefore necessary. The particles should be smaller than 40 $\mu$m (sieve No. 400, USP XIX).

Embolization of the supplying blood vessel leading to a tumor-containing organ or part of an organ ensures isolation from the blood circulation, and the prolamine is then distributed in the entire arterial system, including the capillaries. By the addition of cytostatic agents to the occluding solution according to the invention, it is possible to localize a high dose of the cytostatic agent in the region of the tumor without exposing the RES (reticuloendothelial system) to the cytostatic agent, which is by definition destructive. One can use as cytostatic agents either alkylating substances, such as Melphalan, Dichloren and Triaziquone, or antimetabolites, such as folic acid antagonists, purine antagonists, and pyrimidine antagonists.

The antimicrobial substance can be almost any known drug of this kind, and preferably an antibiotic or a sulphonamide, but also a quaternary ammonium compound. The concentration should be a multiple of the MIC (minimum inhibitory concentration) of the substance for the microorganisms expected in the case of the indication in question (e.g., 1000–10,000 $\mu$g/ml of streptomycin or 5000–50,000 $\mu$g/ml of penicillin G).

To optimize the therapeutic effect aimed at by occluding the ductus pancreaticus in severe pancreatitis, one can add to the solution pancreas inhibitors such as BAEE (benzoyl-1-arginine ethyl ester), TAME (p-toluenesulphonyl-1-arginine methyl ester), inter-$\alpha$-globulin, or serum $\alpha_1$-antitrypsin.

The following examples serve to elucidate the present invention.

EXAMPLE I

Injectable embolizing solutions were prepared from the following components:

| (A) | Ethanol, 60% v/v | 250 ml |
|---|---|---|
| | Sodium amidotrizoate | 60 g |
| | Zein | 70 g |
| | Poppyseed oil | 50 g |
| | Propylene oxide | 4 g |
| (B) | Ethanol, 70%, v/v | 250 ml |
| | Sodium amidotrizoate | 65 g |
| | Zein | 60 g |
| | Peanut oil | 60 g |
| | Propylene oxide | 4 g |
| (C) | Ethanol, 60% v/v | 250 ml |

| -continued | |
|---|---|
| Amidotrizoic acid | 70 g |
| Zein | 60 g |
| Peanut oil | 60 g |
| Propylene oxide | 4 g |

The preparation of solutions A, B, and C started with measuring out the ethanol in the required concentration, after which sodium amidotrizoate or the corresponding free acid was dissolved in it. Instead of the sodium salt, equimolar quantities of the acid and NaOH can also be used. The density and the pH were checked. Zein was added, with careful stirring, and after complete dissolution (12–14 hrs) the viscosity was checked. The oil was then added and emulsified by stirring. The stirring must be done carefully: too intense a stirring leads to the incorporation of air and uncontrolled changes in viscosity. Propylene oxide (PO) was added directly before the solution was poured into ampuls or bottles with a beaded edge. One must make sure here that the temperature of the solution is sufficiently low, in order to prevent evaporation of the propylene oxide and thus uncontrolled variations in its concentration, which could possibly endanger the sterility of the finished solution.

EXAMPLE II

Catheter Embolization of the Arteria Renalis in the Pig

The catheter embolization of the arteria renalis was carried out in the pig with 3.5 ml of a preparation according to the invention (35% w/v of zein in 60% v/v of ethanol and 7% w/w of peanut oil); 34 days later the following findings were obtained:

The histological picture showed a considerable destruction of the renal tissue, affecting the arteries, the medulla, and the renal cortex. In the arterial lumens there were variously large remains of the embolus substance in the course of absorption, the rest being already extensively absorbed.

The absorption occurred through leucocytic agglomerates penetrating the lumen of the vessel in large numbers. The arterial walls were destroyed by leucocyte infiltration and granulation tissue, and their architecture had been completely obliterated. The broad infiltrate and granulation tissue also encroached on the adjacent veins, so that these were similarly destroyed and often unrecognizable. The renal medulla was almost completely covered by granulation tissue and fibrous organization, with massive proliferation of fibroblasts and collagen fiber formation. The system of efferent collecting tubules was extensively obliterated or made atrophic by the fibrous organization, which partly affected the renal cortex as well. In other respects, the renal cortex showed bands of infarct necrosis, already described macroscopically. The destroyed renal tubules already showed calcification in some cases.

The section of the arteria renalis examined separately showed, in the region of the border-shaped wall thickening, similar changes in the blood vessel, with circumscribed necrosis and granulation tissue, inclusion of leucocytes, and proliferation of connective tissue (histological stains: haematoxylin-eosin, PAS reaction, elastica-van Gieson's stain).

Clinical trials have shown that a preoperative embolization of the arteria renalis does not lead to any complications. A controlled closure of the renal artery occurred, which was confirmed on the subsequent operative extirpation of the organ. The operation was greatly facilitated by this preoperative embolization. Loss of blood and a possible escape of tumor cells through the vena renalis were prevented. The embolization and its monitoring on the X-ray screen present no technical difficulties.

Similar results were obtained with the embolizing solutions according to Example I.

We claim:

1. A method for occluding the vascular or duct system of a living organ by injecting into the organ at the site to be occluded a solution comprising prolamine in a physiologically compatible solvent.

2. A method of claim 1 wherein the prolamine is selected from the group consisting of zein, gliadin and hordein.

3. A method of claim 1 wherein the solvent is selected from the group consisting of $C_2$–$C_5$ alcohols, ethylenediamine, 1-acetylpiperidine, ethylene glycol, propylene glycol, glycerol, N-methylacetamide, formamide, hydrazine, dimethylformamide, dimethylsulphoxide, and aqueous solutions thereof.

4. A method of claim 1 wherein the solvent is an aqueous solution of 50 to 96 percent by volume ethanol.

5. A method of claim 4 wherein the prolamine is zein, and the concentration of zein in the solvent is 3 to 60 percent wt/volume.

6. A method of claim 1 wherein the solution has a pH of about 6.5 to 6.8.

7. An injectable embolization and occlusion solution comprising prolamine in a physiologically compatible solvent and from 5 to 45 percent by weight of an emulsified, physiologically compatible oil.

8. A solution of claim 7 wherein said oil is selected from the group consisting of peanut oil, olive oil, poppyseed oil and almond oil.

9. An injectable embolization and occlusion solution comprising prolamine in a physiologically compatible solvent and an X-ray contrast medium.

10. An injectable embolization and occlusion solution comprising prolamine in a physiologically compatible solvent and a radioactive tracer substance.

11. An injectable embolization and occlusion solution comprising prolamine in a physiologically compatible solvent and a cytostatic agent.

12. An injectable embolization and occlusion solution comprising prolamine in a physiologically compatible solvent and an antimicrobial compound.

13. An injectable embolization and occlusion solution comprising prolamine in a physiologically compatible solvent and a specific pancreas inhibitor.

14. A method for occluding the vascular or duct system of a living organ by injecting into the organ at the site to be occluded a solution comprising 5 to 45 percent by wt/volume of zein in 50 to 96 percent by volume aqueous ethanol at a pH of about 6.5 to 6.8.

15. A method of claim 14 wherein the solution has a viscosity of about 350 to 800 centipoise at 25° C.

* * * * *